(12) United States Patent
Borzatta et al.

(10) Patent No.: US 6,342,613 B1
(45) Date of Patent: Jan. 29, 2002

(54) PROCESS FOR THE SYNTHESIS OF 5-(α-HYDROXYALKYL) BENZO[1,3] DIOXOLS

(75) Inventors: Valerio Borzatta, Bologna; Dario Brancaleoni, Sasso Marconi, both of (IT)

(73) Assignee: Endura S.p.A., Bologna (IT)

( * ) Notice: Subject to any disclaimer, the term of this patent is extended or adjusted under 35 U.S.C. 154(b) by 0 days.

(21) Appl. No.: 09/856,752
(22) PCT Filed: Oct. 14, 1999
(86) PCT No.: PCT/EP99/07743
  § 371 Date: May 23, 2001
  § 102(e) Date: May 23, 2001
(87) PCT Pub. No.: WO00/40575
  PCT Pub. Date: Jul. 13, 2000

(30) Foreign Application Priority Data

Dec. 30, 1998 (IT) .......................................... MI98A2857

(51) Int. Cl.⁷ ............................................. C07D 317/50
(52) U.S. Cl. ........................ 549/434; 549/430; 549/445
(58) Field of Search ................................ 549/430, 434, 549/445

(56) References Cited

U.S. PATENT DOCUMENTS

| | | | | |
|---|---|---|---|---|
| 5,514,816 A | * | 5/1996 | Ackermann et al. | ........ 549/212 |
| 5,525,739 A | * | 6/1996 | Andres et al. | ............. 549/434 |
| 5,696,301 A | * | 12/1997 | Harada et al. | ............. 568/763 |

\* cited by examiner

*Primary Examiner*—Floyd D. Higel
*Assistant Examiner*—Golam M. M. Shameem
(74) *Attorney, Agent, or Firm*—Abelman, Frayne & Schwab

(57) ABSTRACT

The present invention regards a three-step process for the synthesis of 5-(α-hydroxyalkyl) benzo[1,3]dioxols. The process comprises: (i) the reaction of pyrocatechin (1,2-dihydroxybenzene) with a dihalo or di-alkoxyalkane, with the formation of a benzo[1,3]dioxol derivative; (ii) 5-selective catalytic acylation of the benzo[1,3]dioxol, with formation of a 5-alkanoylbenzo[1,3]dioxol and its subsequent (iii) reduction to 5-(α-hydroxyalkyl) benzo[1,3]dioxol. Also described are new benzodioxols obtainable using the above-mentioned process. The process of the invention is industrially simple and has low environmental impact; it allows to obtain in high yields derivatives of considerable interest, in particular for the perfumery industry, and in the sector of insecticides.

14 Claims, No Drawings

PROCESS FOR THE SYNTHESIS OF 5-(α-HYDROXYALKYL) BENZO[1,3] DIOXOLS

This application is a 371 of PCT/EP99/07743 filed Oct. 14, 1999.

FIELD OF THE INVENTION

The present invention regards the field of synthesis of benzodioxols, with particular in the perfumery industry and in the sector of insecticides.

PRIOR ART

Various biologically active natural substances, such as flavones and alkaloids contain the methylene dioxy-1,2-benzene (also known as benzo[1,3]dioxol) group. For example, derivatives of benzo[1,3]dioxol are used in the treatment of liver disorders (Chem. Abstracts, 1990, 452534).

The most widespread applications of these derivatives are, however, those in the field of perfumery, flavouring, and insecticides. Compounds having insecticidal action containing the benzo[1,3]dioxol group have been described in various publications (e.g., Bull. Soc. Chim. France, 1964, 1892–1895). 5-(2-propenyl)-benzo[1,3]dioxol (safrole) is a constituent of many essential oils among which oil of sassafras, of which it constitutes approximately 75%. (Oswald et al., Biochim. Biophys. Acta 230, 237 (1971).).

5-(1-propenyl)-benzo[1,3]dioxcl (isosafrole), is an essence used in perfumery and as a deodorant for soaps; isosafrole is in turn used in the synthesis of piperonal (heliotropin, benzo[1,3]dioxol-5-carboxyaldehyde), another essence used industrially for producing perfumes and aromas.

Likewise, also 5-hydroxymethyl-benzo[1,3]dioxol (piperonyl alcohol) and its derivatives are of considerable industrial interest in the sectors cited above. The present invention meets the need of identifying effective methods for the synthesis of piperonyl alcohol and its derivatives.

The prior art describes a number of processes having this purpose. The most widely used method consists in reacting an aldehyde of formula

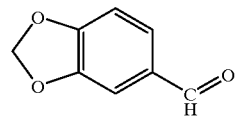

with Grignard reagents, (alkylmagnesium bromides), to obtain benzodioxol derivatives substituted in position 5 with an a-hydroxyalkyl group (see, for example, U.S. Pat. No. 3946040). The same compounds may be obtained starting from 5-keto-substituted derivatives of benzo[1,3]dioxol (DE-A-2210374).

The above processes of synthesis, albeit useful from the analytical standpoint, present significant limitations as regards their industrial applicability. These reactions, in fact, call for the availability of products already containing the benzodioxol cycle: such products are far from being readily available and are very costly. In addition, Grignard reactions are carried out with reagents and anhydrous solvents that are highly unstable and difficult to handle (e.g., magnesium, ethyl ether, tetrahydrofuran), so entailing the adoption of costly safety precautions for the production plants.

Selective acylation, as a means for introducing substituents on the benzodioxol cycle, has so far proved difficult to apply industrially in view of the low yields and the difficulty of purification of the acylated product; for example, in WOA-9639133 the acylated benzodioxol was difficult to purify and involved repeated treatments of decolourization. Other authors have obtained selective acylation of benzodioxols using costly solutions, such as passing the product over a bed of zeolite catalysts (J. Chem. Soc. Chem. Commun., 1994, 717). In view of the limitations pointed out, the need is felt for an effective process for the production of 5-hydroxyalkylbenzodioxols. In particular, a process is sought which is industrially applicable on a wide scale and which may be carried out with reactions that are easy to apply and with a low environmental impact. Finally, the need is felt for a synthetic process that uses as reagents products which are readily available and of low cost.

SUMMARY

The present invention regards a three-step process for the synthesis of 5-(α-hydroxyalkyl)benzo[1,3]dioxols. The process comprises: (i) the reaction of pyrocatechin (1,2-dihydroxybenzene) with a dihalo or di-alkoxyalkane, with the formation of a benzo[1,3]dioxol derivative; (ii) 5-selective catalytic acylation of the benzo[1,3]dioxol derivative, with formation of a 5-alkanoylbenzo[1,3]dioxol and its subsequent (iii) reduction to 5-(α-hydroxyalkyl) benzo[1,3]dioxol. Also described are new benzodioxols obtainable using the above-mentioned process. The process of the invention is industrially simple and has low environmental impact; it allows to obtain in high yields derivatives of considerable interest, in particular for the perfumery industry, and in the sector of insecticides.

DETAILED DESCRIPTION OF THE INVENTION

The subject of the present invention is a new process for the synthesis of 5-(α-hydroxyalkyl)benzo[1,3]dioxols. The process comprises the following steps:

a) reacting 1,2-dihydroxybenzene (pyrocatechin) (I) in a dipolar aprotic solvent, at a temperature comprised between 70° C. and 190° C., with a compound of formula (II), where $R_1$ is chosen from H, and a $C_1$–$C_3$ linear or branched alkyl, and X is chosen from chlorine, fluorine, bromine, iodine, and a $C_1$–$C_5$ linear or branched alkoxy, obtaining the product of formula (III), where $R_1$ has the meanings described above.

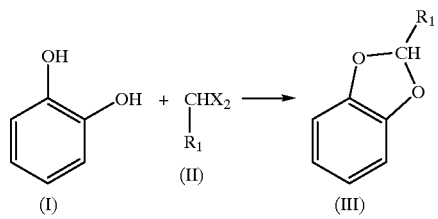

b) Reacting the compound (III) with an aliphatic anhydride of formula (IV) or with an aliphatic acid of formula (V), where $R_2$ is a $C_1$–$C_{19}$ linear or branched alkyl, in the presence of an acylation catalyst, obtaining a compound of formula (VI), where $R_1$ and $R_2$ have the aforesaid meanings.

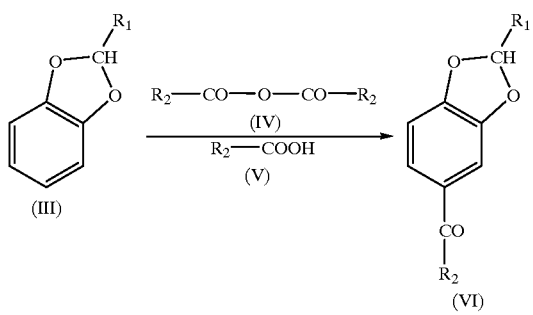

c) Reducing of the compound (VI), obtaining the 5-(α-hydroxyalkyl)benzo[1,3]dioxol of formula (VII)

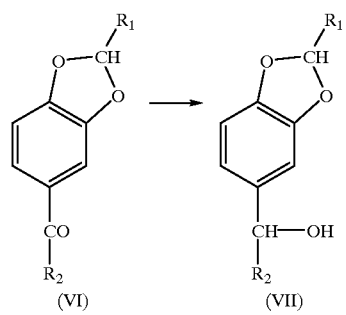

Reaction a) is carried out in dipolar aprotic solvents. Preferred solvents of this type are N,N-dimethylformamide, N,N-dimethylacetamide and dimethylsulphoxide. The temperature of the reaction is that of reflux of the reaction mixture, and is generally between 70° C. and 190° C. In the case where N,N-dimethylformamide is used as reaction solvent, this temperature is generally between 110° C. and 150° C., or more preferably between 110° C. and 130° C. Reaction a) may be carried out in the presence of an iodine salt. In this case, the salt is preferably chosen from among LiI, NaI, KI, CaI$_2$.

The choice of the reagent of formula (II) to be used in reaction a)/depends upon the nature of the final product (VII) that is to be synthesized: if the aim is to obtain benzo[1,3]dioxols not substituted in position 2, reagents of formula (II) will be chosen in which $R_1$=H . Examples of such products are methylene chloride and dimethoxymethane. If the aim is to obtain benzo[1,3]dioxols alkyl-substituted in position 2, the reagent of formula (II) will be chosen in which $R_1$ is the same as the alkyl radical that it is intended to introduce on the benzodioxol ring. Appropriate $R_1$ radicals are methyl, ethyl, n-propyl, and isopropyl.

As has been seen above, the reagent of formula (II) contains two X=halogen groups or else two X=$C_1$–$C_5$ alkoxy groups, either linear or branched. If derivatives of formula (II) are used, where X=halogen, reaction a) is carried out in the presence of an inorganic base, preferably chosen from among NaOH, KOH, Na$_2$CO$_3$, and K$_2$CO$_3$. The inorganic bases of a solid nature (e.g., carbonates) are preferably added to the reaction mixture in a finely ground form.

In the case where derivatives of formula (II) are used, where X=$C_1$–$C_5$ linear or branched alkoxy, reaction a) is carried out in the presence of a transesterification catalyst, preferably chosen from among CH$_3$ONa, C$_2$H$_5$ONa, (C$_4$H$_9$)$_2$SnO, and Ti (OC$_4$H$_9$)$_4$.

Various ways of mixing the aforesaid reagents are possible.

In a preferred embodiment, reaction a) is carried out as follows: Compound (II) is mixed with the dipolar aprotic solvent and with the inorganic base (or transesterification catalyst). To the resulting mixture, heated up to the reflux temperature, pyrocatechin is then added. This addition is preferably made by dripping a liquid mixture obtained by mixing pyrocatechin, derivative (II) and dipolar aprotic solvent.

The mixture thus obtained is heated up to reflux for a period of between 1 and 3 hours, thus terminating the reaction. The final product (III) is separated from the reaction solvent and from the non-reacted derivative (II) by means of fractionated distillation or distillation in a vapour stream.

The reagents are preferably used in the following molar proportions: pyrocatechin : inorganic base : compound (II)= 1:1:2, the said proportion of compound (II) being preferably shared between the initial mixture and the one dripped which contains the pyrocatechin.

The reaction described above leads to the products of formula (III) with yields of more than 90%, typically of around 95%.

The acylation reaction b) leads to the formation of the 5-alkanoylbenzo[1,3]dioxols of formula (VI). This reaction involves the adoption of appropriate acids or anhydrides as acylating agents, and is catalysed preferably by a compound chosen from among ZnO, ZnCl$_2$, FeCl$_2$, FeCl$_3$, FeSO$_4$, Fe$_2$(SO$_4$)$_3$, FeO, Fe$_2$O$_3$, H$_3$PO$_4$, HClO$_4$, and polyphosphoric acid. The particularly preferred catalyst for this reaction is perchloric acid (HClO$_4$). Optionally the reaction takes place in the presence of inert solvents; examples of such solvents are cyclohexane, methylcyclohexane, decalin, dichloroethane, and tetrachloroethane.

In the case where the acid (V) is used as acylating agent, the benzodioxol/acid (V) molar ratio used ranges between 5:1 and 0.5:1, and is preferably 1:1. In the case where the anhydride (IV) is used as acylating agent, the benzodioxol/anhydride (IV) molar ratio ranges between 3:1 and 1:1, and is preferably 2:1.

The reaction temperature is between 0° C. and the boiling point of the most low-boiling component of the reaction mixture.

Various ways of mixing the aforesaid reagents are possible. In a preferred embodiment, the benzo[1,3]dioxol (III) is mixed with the acylation catalyst, and to the mixture the acid or anhydride chosen for the reaction is then added slowly.

The reaction is completed in a period of between 1 and 7 hours. The 5-alkanoylbenzo[1,3]dioxol (VI) is obtained from the reaction mixture by extraction with organic solvent, preferably methylene chloride, and by subsequent fractionated distillation of the organic phase.

In a preferred embodiment, the reaction mixture obtained at the end of step b) undergoes recycling: this process is carried out by adding to the exhausted mixture a fresh amount of the acylation catalyst previously used and a further amount of the acylating agent of formula (IV) or (V); possibly, but not necessarily, a further amount of benzo[1,3]dioxol of formula (III) may be added; these additions are made preferably keeping the molar ratio of benzodioxol and acylating agent within the range of values indicated above.

The mixture thus enriched is then left to react in the same reaction conditions (times and temperature) as those of the first cycle. The said recycling operation may be carried out once or a number of times.

In step c), the 5-alkanoylbenzo[1,3]dioxol (VI) is reduced to 5-(α-hydroxyalkyl)benzo[1,3]dioxol (VII). In general, any reduction reaction may be used in this step. For example, it is possible to use hydrogen in the presence of catalysts such as palladium, platinum or ruthenium. The catalyst may be on an inert matrix substrate: examples of such systems are Pd on carbon, Pt on carbon, Ru on carbon, Pd on alumina, and Pd on barium sulphate. Among the other reduction reagents it is possible to mention $PtO_2$, PtO, Ni-Raney, $NaBH_4$, and $LiAlH_4$.

The reaction conditions (times, temperature, pressure) and the proportions of the reagents are those commonly used in the state of the art for these types of reactions. For example, in the case where gaseous hydrogen on catalyst is used, the operating temperature is preferably between 20° C. and 100° C., with a pressure of between 1 bar and 60 bar, possibly in the presence of an appropriate solvent such as methanol, ethanol, propanol, isopropanol, and butanol.

The process described in the present invention represents the first example of synthesis of 5-(α-hydroxyalkyl)benzo[1,3]dioxols, starting from a non-heterocyclic reagent that is readily available and has a low cost (pyrocatechin). The high yield obtainable in the three steps of the reaction described above enables large quantities of final product to be obtained.

Reaction step a) moreover enables 2-alkyl-substituted benzo[1,3]dioxols to be obtained, without resorting to a separate alkylation step in position 2.

The 2-alkyl-substituted products obtainable by means of the process described above are new and as such constitute a further aspect of the present invention.

These compounds have the formula of structure (VIII):

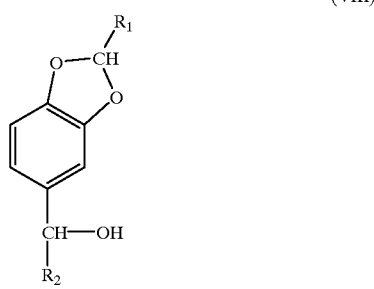

(VIII)

where $R_1$ is chosen from among $C_1$–$C_3$ linear or branched alkyl, and $R_2$ is a $C_1$–$C_{19}$ alkyl, either linear or branched alkyl.

A preferred group of products of formula VIII is the one in which R1 represents methyl, ethyl, n-propyl, and isopropyl.

The derivatives of formula (VII), irrespective of whether they are substituted or not in position 2 on the benzo[1,3]dioxol ring, in addition to being of interest on their own account as essences and aromas, are also usable as reagents in the preparation of similar derivatives, and are of particular interest for the perfumery industry or in the production of insecticides. The preferred example of these compounds is represented by the 5-alkylbenzo[1,3]dioxols, and in particular by 5-propylbenzo[1,3]dioxol (dihydrosafrole). The present invention thus includes also the preparation of these products, which are obtained by subjecting the derivatives of formula (VII), previously obtained by means of step c), to a further reduction. The 5-alkylbenzo[1,3]dioxols may also be obtained directly with a single reduction reaction starting from the compounds of formula (VI). Proceeding in this way, the derivatives of formula (VII) are formed as intermediates, but are not isolated: in this case it is preferable to use, as reduction catalysts, metals on an inert substrate, such as Pd/C, Pt/C, and $Pd/BaSO_4$.

5-(1-propenyl)-benzo[1,3]dioxol, (isosafrole) is another example of a derivative obtainable through the process that forms the subject of the present invention. In this case, the 5-hydroxyalkylbenzo[1,3]dioxols of formula VII) obtained in step c) undergo dehydration reactions. Such dehydration reactions, which are in themselves known in the literature, may be carried out in the presence of a suitable solvent, such as benzene, toluene, xylene, mesithylene, dichloroethane, and tetrachloroethane, in the presence of an organic or inorganic acid, such as, for example, nitric acid, sulphuric acid, hydrochloric acid, perchloric acid, acetic acid, trifluoroacetic acid, benzenesulphonic acid, and p-toluenesulphonic acid at the boiling temperature of the solvent, and by removing the reaction water by means of azeotropation.

5-(1-propenyl)-benzo[1,3]dioxol is in turn convertible into piperonal, or else, by means of a further reduction reaction, into 5-propylbenzo[1,3]dioxol (dihydrosafrole).

The invention in question is illustrated in the sequel by the following non-limiting examples.

EXPERIMENTAL PART

1. Preparation of benzo[1,3]dioxol

To a mixture of 104 g (0.75 mol) of potassium carbonate finely ground in 440 ml of N,N-dimethylformamide were added 45 ml (0.7 mol) of methylene chloride, and the mixture thus obtained was heated up to the reflux temperature (128–130° C.). Then a solution of 75 g (0.68 mol) of pyrocatechin dissolved in 110 ml of N,N-dimethylformamide and 45 ml (0.7 mol) of methylene chloride was added drop by drop.

At the end of dripping, the mixture was heated up to reflux for a further 2 hours, cooled and then filtered. The solution thus obtained was distilled at room pressure, and 42 ml of dichloromethane were collected (40–41° C.). To this was subsequently added, at portions of 50 ml each, 400 ml of water, distilling at 98–100° C. an azeotrope consisting of benzo[1,3]dioxol and water, and, finally distilling the N,N-dimethylformamide at 152–153° C.

From the mixture of benzo[1,3]dioxol and water was separated the product, and the aqueous phase was added with a saturated solution of sodium chloride, followed by two extractions with 60 ml of dichloromethane.

The product and the organic solution were reunited, evaporated at 25° C./20 mbar, obtaining 78 g of benzo[1,3]dioxol.

2. Preparation of 5-propanoylbenzo[1,3]dioxol

To a mixture of 73.2 g (0.6 mol) of benzo[1,3]dioxol and 1 ml of 70% perchloric acid, cooled to 0–5° C., were slowly added 38.1 ml (0.3 mol) of propionic anhydride, keeping the temperature at 0–5° C. during the addition.

Once the addition was complete, the mixture was left under stirring for a further 3 hours, allowing the temperature to rise to room temperature. The mixture was diluted with 50 ml of dichloromethane and 50 ml of water, stirred for half an hour, and the organic phase was then separated. The organic phase was washed with 30 ml of sodium hydroxide 2M aqueous solution and with water, and, finally dried on sodium sulphate.

The organic phase was distilled at room pressure, collecting the dichloromethane at 40–41° C., distilling the benzo

[1,3]dioxol that had not reacted (44 g) at 55° C./1.3 mbar and, finally, the product (34.5 g) at 125–130° C./1.3 mbar.

To the reaction mixture containing the 44 g of non-reacted benzo[1,3]dioxol were added 29.2 g (0.24 mol) of benzo[1.3]dioxol and 1 ml of 70% perchloric acid. To the resulting mixture, cooled to 0–5° C., was added 38.1 ml (0.3 mol) of propionic anhydride. Using the method described in the previous paragraph, 44 g of non-reacted benzo[1,3]dioxol and 34.5 g of the desired product were isolated.

3. Preparation of 5-(α-hydroxypropyl)benzo[1,3]dioxol

Into a 250-ml multiple-necked flask were introduced, under nitrogen flow, 30 g of 5-propanoylbenzo[1,3]dioxol (0.268 mol) dissolved in 100 ml of methanol. At 25° C., 7 g of NaBH$_4$ (0.185 mol) dissolved in 50 ml of methanol were dripped in 20 minutes; then the reaction mixture was brought to reflux. After 2 hours the mixture was cooled, the methanol was removed at reduced pressure, and the mixture was diluted with 100 ml of HCl 2M and extracted twice with CH$_2$Cl$_2$. The reunited organic phases were washed with 100 ml of H$_2$O and concentrated at reduced pressure to obtain 30.07 g of dense, clear oil, the analysis of which—GC, MS, NMR ($^1$H, $^{13}$C, DEPT)—was in conformity with the desired product. Alternatively, 5-(α-hydroxypropyl)benzo[1,3]dioxol was prepared as follows: Into a 1-litre autoclave, 30 g of 5-propanoylbenzo[1,3]dioxol (0.168 mol) dissolved in 150 ml of isopropanol and 1 g of Ru/C 5% were poured. The autoclave was closed, rendered inert with nitrogen, and brought to the pressure of 1 bar with H$_2$ under stirring. The mixture was left under stirring with H$_2$ pressure constant at 1 bar for 1 hour; then it was washed with N$_2$ and filtered. By evaporation of the solvent at reduced pressure, 30 g of a dense oil were obtained, the analysis of which—GC, MS, NMR ($^1$H, $^{13}$C, DEPT)—was in conformity with the desired product.

Preparation of 5-propylbenzo[1,3]dioxol (dihydrosafrole)

34.5 g of 5-propanoylbenzo[1,3]dioxol (0.19 mol) were dissolved in 100 ml of isopropanol, and 2 g of 50% wet Pd/C 5% were added.

The mixture was put into an autoclave and hydrogenated at a pressure of 4 bar and a temperature of 40° C.

The mixture was filtered, and evaporated at 40° C./20 mbar, to obtain an oil (31 g), which was distilled at 108–109° C./18 mbar, the analysis of which—GC, MS, NMR ($^1$H, $^{13}$C, DEPT)—was in conformity with the desired product.

5. Preparation of 5-[(E) 1-propenyl]-1,3-benzodioxol

Into a 100-ml multiple-necked flask were introduced 5 g of 5-(α-hydroxyethyl)benzo[1,3]dioxol (27 mmol) dissolved in 50 ml of toluene and a crystal of p-toluenesulphonic acid. The reaction mixture was brought to reflux, and the water formed by the reaction was collected by azeotropation. After 2 hours, 10 ml of NaOH 2M were added to the cooled mixture, and the mixture was left under stirring for 15 minutes. Once the two phases had been separated, the organic phase was concentrated at reduced pressure obtaining a yellow oil, which was purified by distillation (90° C., 1 mmHg).

4.1 g of clear, yellowish oil were obtained, the analysis of which—GC, MS, NMR, ($^1$H, $^{13}$C, DEPT)—was in conformity with the desired product.

What is claimed is:
1. A process for the synthesis of 5-(α-hydroxyalkyl)benzo[1,3]dioxols, comprising the following steps:
   a) reacting the 1,2-dihydroxybenzene (pyrocatechin) (I) in a dipolar aprotic solvent at a temperature of between 70° C. and 190° C., with a compound of formula (II), where R$_1$ is chosen from H, a C$_1$–C$_3$, linear or branched alkyl, and X is chosen from chlorine, fluorine, bromine, iodine, and a C$_1$–C$_5$ linear or branched alkoxy, obtaining the product of formula (III), where R$_1$ has the meanings described above,

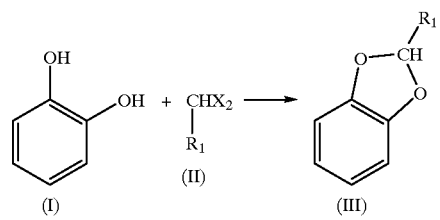

b) reacting the compound (III) with an aliphatic anhydride of formula (IV) or with an aliphatic acid of formula (V), where R$_2$ is a C$_1$–C$_{19}$ linear or branched alkyl, in the presence of an acylation catalyst, obtaining a compound of formula (VI), where R$_1$ and R$_2$ have the aforesaid meanings,

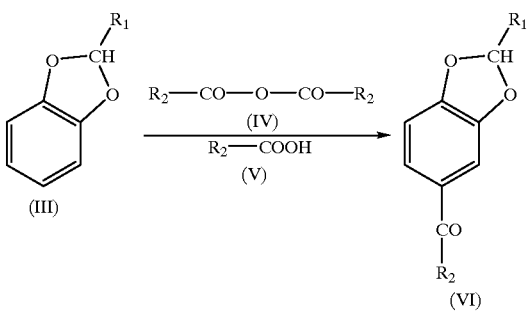

c) reducing compound (VI), obtaining the 5-(α-hydroxyalkyl)benzo[1,3]dioxol of formula (VII)

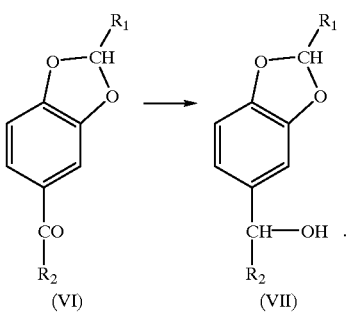

2. The process according to claim 1, wherein the dipolar aprotic solvent used in reaction a) is chosen from N,N-diethylformamide, N,N-dimethylacetamide, and dimethylsulphoxide.

3. The process according to claim 1, wherein reaction a) is carried out in the presence of an iodine salt.

4. The process according to claim 1, wherein the reaction b) is catalysed by a compound chosen from HClO$_4$, ZnO, ZnCl$_2$, FeCl$_2$, FeCl$_3$, FeSO$_4$, Fe$_2$(SO$_4$)$_3$, FeO, Fe$_2$O$_3$, H$_3$PO$_4$, and polyphosphoric acid.

5. The process according to claim 1, wherein reaction b) takes place in the presence of inert solvents.

6. The process according to claim 1, wherein reaction b) the benzodioxol/acid (V) molar ratio is between 5:1 and 0.5:1.

7. The process according to claim 1, wherein reaction b) the benzodioxol/anhydride (IV) molar ratio is between 3:1 and 1:1.

8. The process according to claim 1, wherein the reaction mixture resulting from reaction b) undergoes recycling.

9. The process according to claim 1, wherein the derivative of formula (VII) is subjected to further reduction, with the formation of a 5-alkylbenzo[1,3]dioxol.

10. The process according to claim 9, wherein the derivative of formula (VII) is 5-(α-hydroxypropyl)benzo[1,3]dioxol, and the said 5-alkylbenzo[1,3]dioxol is 5-propylbenzo[1,3]dioxol (dihydrosafrole).

11. The process according to claim 1, wherein the derivative of formula (VII) is further subjected to dehydration, with the formation of a 5-(1-alkenyl)benzo[1,3]dioxol.

12. The process according to claim 11, wherein the derivative of formula (VII) is 5-(α-hydroxypropyl)benzo[1,3]dioxol and the said 5-(1-alkenyl)benzo[1,3]dioxol is 5-(1-propenyl)benzo[1,3]dioxol (isosafrole).

13. The compounds of formula (VIII)

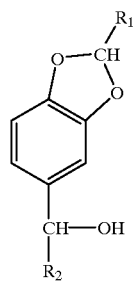

(VIII)

where $R_1$ is chosen from $C_1$–$C_3$ linear or branched alkyl, and $R_2$ is a $C_1$–$C_{19}$ linear or branched alkyl.

14. The compounds according to claim 13, where $R_1$ represents methyl, ethyl, n-propyl, or isopropyl.

* * * * *